United States Patent
Marodon et al.

(10) Patent No.: US 9,695,247 B2
(45) Date of Patent: Jul. 4, 2017

(54) ANTIBODIES DIRECTED AGAINST ICOS FOR TREATING GRAFT-VERSUS-HOST DISEASE

(71) Applicants: INSERM (INSTITUT NATIONAL DE LA SANTE ET DE LA RECHERCHE MEDICALE), Paris (FR); CENTRE LEON BERARD, Lyons (FR); UNIVERSITÉ D'AIX-MARSEILLE, Marseilles (FR)

(72) Inventors: Gilles Marodon, Paris (FR); Daniel Olive, Marseilles (FR); Christine Menetrier-Caux, Lyons (FR)

(73) Assignees: INSERM (INSTITUT NATIONAL DE LA SANTE ET DE LA RECHERCHE MEDICALE), Paris (FR); CENTRE LEON BERARD, Lyons (FR); UNIVERSITÉ D'AIX-MARSEILLE, Marseilles 7 (FR)

( * ) Notice: Subject to any disclaimer, the term of this patent is extended or adjusted under 35 U.S.C. 154(b) by 309 days.

(21) Appl. No.: 14/424,092

(22) PCT Filed: Sep. 3, 2013

(86) PCT No.: PCT/EP2013/068199
§ 371 (c)(1),
(2) Date: Feb. 26, 2015

(87) PCT Pub. No.: WO2014/033327
PCT Pub. Date: Mar. 6, 2014

(65) Prior Publication Data
US 2015/0239978 A1 Aug. 27, 2015

(30) Foreign Application Priority Data
Sep. 3, 2012 (EP) .................... 12306046

(51) Int. Cl.
C07K 16/28 (2006.01)
A61K 39/395 (2006.01)
A61K 39/00 (2006.01)

(52) U.S. Cl.
CPC ...... *C07K 16/2896* (2013.01); *C07K 16/2818* (2013.01); *A61K 2039/505* (2013.01); *C07K 2317/565* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| 7,465,445 | B2 | 12/2008 | Tezuka et al. |
| 9,376,493 | B2 * | 6/2016 | Faget ................. C07K 16/2818 |
| 2011/0243929 | A1 | 10/2011 | Coyle et al. |
| 2011/0293605 | A1 | 12/2011 | Sathish et al. |
| 2016/0264666 | A1 * | 9/2016 | Faget ................. C07K 16/2818 |

OTHER PUBLICATIONS

Tajima et al., "JTA-009, a fully human antibody against human AILIM/ICOS, ameliorates graft-vs-host reaction in SCID mice grafted with human PBMCs", Experimental Hematology, Nov. 1, 2008, pp. 1514-1523, vol. 36, No. 11, Elsevier, Inc.
Sulaiman et al., "Multiple combination therapies involving blockade of ICOS/B7RP-1 costimulation facilitate long-term islet allograft survival", American Journal of Transplantation, Apr. 1, 2004, pp. 526-536, vol. 4, No. 4, Blackwell Munksgaard, DK.

* cited by examiner

*Primary Examiner* — Ilia Ouspenski
(74) *Attorney, Agent, or Firm* — Whitham, Curtis & Cook, P.C.

(57) ABSTRACT

The invention relates to a specific antibody directed against, for use for treating graft versus host disease.

6 Claims, 3 Drawing Sheets

ANTIBODIES DIRECTED AGAINST ICOS FOR TREATING GRAFT-VERSUS-HOST DISEASE

FIELD OF THE INVENTION

The invention relates to the use of antibodies directed against ICOS in the treatment of graft-versus-host disease.

BACKGROUND OF THE INVENTION

Graft versus Host Disease (GVHD) is a major debilitating, and potentially lethal, side effect of bone marrow transplantation. It occurs when lymphocytes from the donor present in the bone marrow inoculums attack and destroy healthy tissues of the recipient. It is thought that GVHD is however useful to eliminate residual tumors persisting after chemical treatments. Biological means to better manage GVHD will therefore have a major impact on public health.

Among numerous costimulatory signals necessary for T cell activation, the inhibition of ICOS-LICOS interaction has been shown to prevent or delay GVHD in mice models (Taylor et al. (2005) Blood 105(8): 3372-3380).

The current treatments for GVHD are intravenously administered glucocorticoids, such as prednisone. The use of these glucocorticoids is designed to suppress the T-cell-mediated immune onslaught on the host tissues; however, in high doses, this immune-suppression raises the risk of infections and cancer relapse.

Therefore, there is still a great need for providing efficient therapeutic strategies targeting GVHD, with lower side effects.

The inventors surprisingly found that a monoclonal antibody against human ICOS, called 314.8, significantly impacts a xenogenic GVHD (xeno-GVHD) induced after transfer of human cells into immunodeficient mice. Xeno-GVHD is a closer model of GVHD than mice models relative to the human disease. Thus, said antibody may constitute a promising therapeutic strategy of GVHD.

SUMMARY OF THE INVENTION

The present invention relates to an antibody directed against ICOS, having the following 6 CDRs, for use for treating GVHD:

|        | Aminoacid sequence              |
|--------|---------------------------------|
| H-CDR1 | GYTFTTYWMH (SEQ ID NO: 7)       |
| H-CDR2 | EIDPSDSYVNYNQNFKG (SEQ ID NO: 8)|
| H-CDR3 | FDY (SEQ ID NO: 9)              |
| L-CDR1 | RSSKSPLHSNGNIYLY (SEQ ID NO: 10)|
| L-CDR2 | RMSNLAS (SEQ ID NO: 11)         |
| L-CDR3 | MQHLEYPYT (SEQ ID NO: 12)       |

Preferably, said antibody is selected from the group consisting of Icos 314-8, obtainable from the hybridoma deposited at the "Collection Nationale de Cultures de Microorganismes" (CNCM, Institut Pasteur, 25 rue du Docteur Roux, 75724 Paris Cedex 15, France), in accordance with the terms of Budapest Treaty, on Jul. 2, 2009 under the accession number CNCM 1-4180, its conservative fragments and its conservative derivatives.

DETAILED DESCRIPTION OF THE INVENTION

Definition

As used herein, the terms "ICOS" or "Inductible T cell costimulator" refer to a transmembrane homodimeric glycoprotein of 55 to 60 kDa which presents an IgV type domain in its extracellular part and a tyrosine within an YMFM motif in its cytoplasmic part. It has been shown that ICOS engagement with its ligand induces the phosphorylation of the tyrosine in the cytoplasmic part of ICOS. Said phosphorylation is responsible for the recruitment of the p85 PI3K regulatory subunit, which activates the PI3K/AKT signaling pathway.

ICOS engagement is also described to induce the expression of CD40L at the cell surface. CD40L is known to have an important effect in the cooperation between T lymphocytes and B lymphocytes.

ICOS has been found to be expressed, following TCR activation, on conventional T cells (Tconv CD4+, CD8+ subsets) as well as on Treg.

As used herein, the terms "ICOSL", "ICOS-L" and "B7-H2" refer to an ICOS ligand. Said ligand is present on lymphoid cells such as B lymphocytes, macrophages, dendritic cells, as well as on non-lymphoid cells such as endothelial or epithelial cells. ICOS engagement has an important role in the lymphocyte activation, and it induces the proliferation and survival of T lymphocytes, especially Treg.

As used herein, the term "JICOS 1" refers to a specific cell line expressing ICOS.

As used herein, a "monoclonal antibody" in its various grammatical forms refers to a population of antibodies that contains only one species of antibody combining sites capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody. Although historically a monoclonal antibody was produced by immortalization of a clonally pure immunoglobulin secreting cell line, a monoclonally pure population of antibody molecules can also be prepared by the methods of the present invention. Laboratory methods for preparing monoclonal antibodies are well known in the art (see, for example, Harlow et al., 1988). Monoclonal antibodies (mAbs) may be prepared by immunizing purified mutated TXAS into a mammal, e.g. a mouse, rat, human and the like mammals. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975). While mAbs can be produced by hybridoma culture the invention is not to be so limited. Also contemplated is the use of mAbs produced by an expressing nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; PCT Publication No.; European Patent Publications No. 0239400 to Winter et al. and No. 0125023 to Cabilly et al. Antibody generation techniques not involving immunisation are also contemplated such as for example using phage display technology to examine naive libraries (from non-immunised animals); see Barbas et al. (1992), and Waterhouse et al. (1993).

As used herein, the expression "fragment of an antibody" refers to a portion of said antibody comprising at least the antigen-binding domain. Said fragments are for example a Fab, Fab', F(ab')2, Fv.

As used herein, the expression "derivative of an antibody" refers to an antibody which comprises the 6 CDRs of said antibody.

By conservative fragments of 314.8 mAb and conservative derivatives of 314.8 mAb, it is respectively meant fragments and derivatives which retain the binding affinity and specificity of 314.8 for ICOS. The fragment may be a portion of said antibody, like a heavy chain, a light chain, a VL, a VH, a Fab, a Fab', a F(ab)2, F(ab')2, or dAb, but also any minimum unit consisting of amino acid residues that mimic the hypervariable region, such as a CDR (CDR1H, CDR2H, CDR3H, CDR1L, CDR2L, CDR3L). The conservative fragments of the invention also comprise dAbs. dAbs (single domain antibodies) are antibodies which comprise only one protein chain which derives from one of the two domains of the normal structure of an antibody. Indeed, in certain cases, half of an antibody can bind its target antigen with an affinity comparable to the affinity of the wild-type antibody. The conservative fragments according to the invention can be produced using methods well known in the prior art. Such fragments can be obtained by routine methods, such as a proteolytic digestion (for example, pepsin digestion to generate F(ab')2; digestion with papain to generate Fab).

As used herein, the expression "314.8 mAb" or "Icos 314-8" or "Icos R 314-8" refers to a monoclonal antibody directed against ICOS deposited to CNCM on Jul. 2, 2009 under the accession number CNCM I-4180.

The 6 CDRs of 314.8 mAb are as in Table 1 below:

TABLE 1

|  | DNA sequence | Aminoacid sequence |
|---|---|---|
| H-CDR1 | GGCTACACCTTCACCACCTACT GGATGCAC (SEQ ID NO: 1) | GYTFTTYWMH (SEQ ID NO: 7) |
| H-CDR2 | GAGATTGATCCTTCTGATAGTT ATGTTAACTACAATCAAAACTT TAAGGGC (SEQ ID NO: 2) | EIDPSDSYVNYNQNFKG (SEQ ID NO: 8) |
| H-CDR3 | TTTGATTAC (SEQ ID NO: 3) | FDY (SEQ ID NO: 9) |
| L-CDR1 | AGGTCTAGTAAGAGTCCCCTGC ATAGTAACGGCAACATTTACTT ATAT (SEQ ID NO: 4) | RSSKSPLHSNGNIYLY (SEQ ID NO: 10) |
| L-CDR2 | CGGATGTCCAACCTTGCCTCA (SEQ ID NO: 5) | RMSNLAS (SEQ ID NO: 11) |
| L-CDR3 | ATGCAACATCTAGAATATCCG TACACG (SEQ ID NO: 6) | MQHLEYPYT (SEQ ID NO: 12) |

The complete sequences of the variable regions (VH and VL) of mAb 314.8 are the following:

```
Heavy chain: DNA sequence (426 bp): Leader sequence-FR1-CDR1-FR2-
CDR2-FR3-CDR3-FR4
                                                    (SEQ ID NO: 13)
ATGGGATGGCGCTGTATCATCCTCTTCTTGGTATCAACAGCTACAGGTGTCCACTCCCAGGTCC

AACTACAGCAGCCTGGGACTGAACTTATGAAGCCTGGGGCTTCAGTGAAGCTGTCCTGCAAGGC

TTCTGGCTACACCTTCACCACCTACTGGATGCACTGGGTGAAGCAGAGGCCTGGACAAGGCCTT

GAGTGGATCGGAGAGATTGATCCTTCTGATAGTTATGTTAACTACAATCAAAACTTTAAGGGCA

AGGCCACATTGACTGTAGACAAATCCTCCAGCACAGCCTACATACAGCTCAGCAGCCTGACATC

TGAGGACTCTGCGGTCTATTTTTGTGCGAGATCCCCTGATTACTACGGTACTAGTCTTGCCTGG

TTTGATTACTGGGGCCAAGGGACTCTGGTCACTGTCTCTACA

Heavy chain: Amino acids sequence (142 AA): Leader sequence-FR1-
CDR1-FR2-CDR2-FR3-CDR3-FR4
                                                    (SEQ ID NO: 14)
MGWRCIILFLVSTATGVHSQVQLQQPGTELMKPGASVKLSCKASGYTFTTYWMHWVKQRPGQGL

EWIGEIDPSDSYVNYNQNFKGKATLTVDKSSSTAYIQLSSLTSEDSAVYFCARSPDYYGTSLAW

FDYWGQGTLVTVST

Light chain: DNA sequence (396 bp): Leader sequence-FR1-CD1-FR2-
CDR2-FR3-CDR3-FR4
                                                    (SEQ ID NO: 15)
ATGAGGTGCCTAGCTGAGTTCCTGGGGCTGCTTGTGCTCTGGATCCCTGGAGTCATTGGGATA

TTGTGATGACTCAGGCTGCACCCTCTGTACCTGTCACTCCTGGAGAGTCAGTATCCATCTCCTG
```

```
CAGGTCTAGTAAGAGTCCCCTGCRTAGTAACGGCAACATTTACTTATATTGGTTCCTGCAGAGG

CCAGGCCAGTCTCCTCAGCTCCTGATATATCGGATGTCCAACCTTGCCTCAGGAGTCCCAGACA

GGTTCAGTGGCAGTGGGTCAGGAACTACTTTCACACTGAAAATCAGTAGAGTGGAGGCTGAGGA

TGTGGGTGTTTATTACTGTATGCAACATCTAGAATATCCGTACACGTTCGGAGGGGGACCAAG

CTGGAAATAAAA

Light chain: Amino acids sequence (132 AA): Leader sequence-FR1-
CDR1-FR2-CDR2-FR3-CDR3-FR4
                                                    (SEQ ID NO: 16)
MRCLAEFLGLLVLWIPGVIGDIVMTQAAPSVPVTPGESVSISCRSSKSPLHSNGNIYLYWFLQR

PGQSPQLLIYRMSNLASGVPDRFSGSGSGTTFTLKISRVEAEDVGVYYCMQHLEYPYTFGGGTK

LEIK
```

The present invention also refers to antibodies comprising SEQ ID NO:18 in their heavy chain and SEQ ID NO:20 in their light chain. It also refers to antibodies encoded by at least nucleotidic sequences SEQ ID NO:17 for the heavy chain and SEQ ID NO:19 for the light chain:

the acute or fulminant form of the disease (aGVHD) is normally observed within the first 100 days post-transplant, and is a major challenge to transplants owing to associated morbidity and mortality;

```
Heavy chain: DNA sequence: FR1-CDR1-FR2-CDR2-FR3-CDR3-FR4
                                                    (SEQ ID NO: 17)
CAGGTCCAACTACAGCAGCCTGGGACTGAACTTATGAAGCCTGGGGCTTCAGTGAAGCTGTCCT

GCAAGGCTTCTGGCTACACCTTCACCACCTACTGGATGCACTGGGTGAAGCAGAGGCCTGGACA

AGGCCTTGAGTGGATCGGAGAGATTGATCCTTCTGATAGTTATGTTAACTACAATCAAAACTTT

AAGGGCAAGGCCACATTGACTGTAGACAAATCCTCCAGCACAGCCTACATACAGCTCAGCAGCC

TGACATCTGAGGACTCTGCGGTCTATTTTTGTGCGAGATCCCCTGATTACTACGGTACTAGTCT

TGCCTGGTTTGATTACTGGGGCCAAGGGACTCTGGTCACTGTCTCTACA

Heavy chain: Amino acids sequence: FR1-CDR1-FR2-CDR2-FR3-CDR3-FR4
                                                    (SEQ ID NO: 18)
QVQLQQPGTELMKPGASVKLSCKASGYTFTTYWMHWVKQRPGQGLEWIGEIDPSDSYVNYNQNF

KGKATLTVDKSSSTAYIQLSSLTSEDSAVYFCARSPDYYGTSLAWFDYWGQGTLVTVST

Light chain: DNA sequence: FR1-CDR1-FR2-CDR2-FR3-CDR3-FR4
                                                    (SEQ ID NO: 19)
GATATTGTGATGACTCAGGCTGCACCCTCTGTACCTGTCACTCCTGGAGAGTCAGTATCCATCT

CCTGCAGGTCTAGTAAGAGTCCCCTGCATAGTAACGGCAACATTTACTTATATTGGTTCCTGCA

GAGGCCAGGCCAGTCTCCTCAGCTCCTGATATATCGGATGTCCAACCTTGCCTCAGGAGTCCCA

GACAGGTTCAGTGGCAGTGGGTCAGGAACTACTTTCACACTGAAAATCAGTAGAGTGGAGGCTG

AGGATGTGGGTGTTTATTACTGTATGCAACATCTAGAATATCCGTACACGTTCGGAGGGGGAC

CAAGCTGGAAATAAAA

Light chain: Amino acids sequence: FR1-CDR1-FR2-CDR2-FR3-CDR3-FR4
                                                    (SEQ ID NO: 20)
DIVMTQAAPSVPVTPGESVSISCRSSKSPLHSNGNIYLYWFLQRPGQSPQLLIYRMSNLASGVP

DRFSGSGSGTTFTLKISRVEAEDVGVYYCMQHLEYPYTFGGGTKLEIK
```

Preferably, the antibodies of the invention are chosen from 314.8 mAb, its conservative fragments and its conservative derivatives.

Graft-versus-host disease (GVHD) is a common complication following an allogeneic tissue transplant. It is commonly associated with stem cell or bone marrow transplant. GVHD can also occur after a blood transfusion if irradiated blood products are not used.

As used herein, graft-versus-host-disease is divided into acute and chronic forms:

the chronic form of graft-versus-host-disease (cGVHD) normally occurs after 100 days. The appearance of moderate to severe cases of cGVHD adversely influences long-term survival.

This distinction is not arbitrary: acute and chronic graft-versus-host-disease appear to involve different immune cell subsets, different cytokine profiles and somewhat different host targets.

As used herein, the terms "treating" or "treatment" means reversing, alleviating, inhibiting the progress of, or preventing the disorder or condition to which such term applies, or one or more symptoms of such disorder or condition.

A "therapeutically effective amount" is intended for a minimal amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

As used herein, the term "prevention" refers to alleviating the disease or condition from occurring in a subject which has not yet been diagnosed as having it. As used herein, the term "subject" denotes a mammal, such as a rodent, a feline, a canine, and a primate. Preferably a subject according to the invention is a human.

The present invention relates to an antibody directed against ICOS, having the following 6 CDRs, for use for treating GVHD:

|  | Aminoacid sequence |
|---|---|
| H-CDR1 | GYTFTTYWMH (SEQ ID NO: 7) |
| H-CDR2 | EIDPSDSYVNYNQNFKG (SEQ ID NO: 8) |
| H-CDR3 | FDY (SEQ ID NO: 9) |
| L-CDR1 | RSSKSPLHSNGNIYLY (SEQ ID NO: 10) |
| L-CDR2 | RMSNLAS (SEQ ID NO: 11) |
| L-CDR3 | MQHLEYPYT (SEQ ID NO: 12) |

Preferably, said antibody is selected from the group consisting of Icos 314-8, obtainable from the hybridoma deposited at the "Collection Nationale de Cultures de Microorganismes" (CNCM, Institut Pasteur, 25 rue du Docteur Roux, 75724 Paris Cedex 15, France), in accordance with the terms of Budapest Treaty, on Jul. 2, 2009 under the accession number CNCM 1-4180, its conservative fragments and its conservative derivatives.

Nucleic Acid Sequence Encoding an Antibody of the Invention

A further embodiment of the invention relates to an antibody directed against ICOS for use for treating GVHD, wherein the nucleotidic sequences encoding the 6 CDRs of said antibody are the following:

|  | DNA sequence |
|---|---|
| H-CDR1 | GGCTACACCTTCACCACCTACTGGATGCAC (SEQ ID NO: 1) |
| H-CDR2 | GAGATTGATCCTTCTGATAGTTATGTTAAC TACAATCAAAACTTTAAGGGC (SEQ ID NO: 2) |
| H-CDR3 | TTTGATTAC (SEQ ID NO: 3) |
| L-CDR1 | AGGTCTAGTAAGAGTCCCCTGCATAGTAAC GGCAACATTTACTTATAT (SEQ ID NO: 4) |

-continued

|  | DNA sequence |
|---|---|
| L-CDR2 | CGGATGTCCAACCTTGCCTCA (SEQ ID NO: 5) |
| L-CDR3 | ATGCAACATCTAGAATATCCGTACACG (SEQ ID NO: 6) |

In a particular embodiment, the invention relates to a nucleic acid sequence encoding the VH domain or the VL domain of one of the antibodies selected from the group consisting of 314.8 mAb, its conservative fragments and its conservative derivatives.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. So, a further object of the invention relates to a vector comprising a nucleic acid of the invention. Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40, LTR promoter and enhancer of Moloney mouse leukemia virus, promoter and enhancer of immunoglobulin H chain and the like.

Any expression vector for animal cell can be used, so long as a gene encoding the human antibody C region can be inserted and expressed. Examples of suitable vectors include pAGE107, pAGE103, pHSG274, pKCR, pSG1 beta d2-4- and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present invention relates to a cell which has been transfected, infected or transformed by a nucleic acid and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed". The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g. Vero cells, CHO cells, 3T3 cells, COS cells, etc.) as well as primary or established mammalian cell cultures (e.g. produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective, rat YB2/3HL.P2.G11.16Ag.20 cell (ATCC CRL1662, hereinafter referred to as "YB2/0 cell"), and the like.

The present invention also relates to a method of producing a recombinant host cell expressing an antibody according to the invention, said method comprising the steps of:

(i) introducing in vitro or ex vivo a recombinant nucleic acid or a vector as described above into a competent host cell, (ii) culturing in vitro or ex vivo the recombinant host cell obtained, and (iii) optionally, selecting the cells which express and/or secrete said antibody. Such recombinant host cells can be used for the production of antibodies of the invention.

Pharmaceutical Composition According to the Invention

The invention also relates to pharmaceutical compositions comprising an antibody of the invention.

Therefore, an antibody of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment. To prepare pharmaceutical compositions, an effective amount of the antibody may be dissolved or dispersed in a pharmaceutically acceptable carrier or aqueous medium. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose.

These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 A, containing an aqueous solution in the core. The physical characteristics of liposomes depend on pH, ionic strength and the presence of divalent cations.

Method for Producing Antibodies of the Invention

Antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In particular, the invention further relates to a method of producing an antibody of the invention, which method comprises the steps consisting of:

(i) culturing a transformed host cell according to the invention under conditions suitable to allow expression of said antibody; and (ii) recovering the expressed antibody.

In another particular embodiment, the method comprises the steps of:

(i) culturing the hybridoma deposited as CNCM I-4180 under conditions suitable to allow expression of the antibody; and (ii) recovering the expressed antibody.

Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used. Methods for producing chimeric antibodies involve conventional recombinant DNA and gene transfection techniques are well known in the art (See patent documents U.S. Pat. Nos. 5,202,238; and 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred. Examples of tandem type humanized antibody expression vector include pKANTEX93 (WO 97/10354), pEE18 and the like.

Methods for producing humanized antibodies based on conventional recombinant DNA and gene transfection techniques are well known in the art. Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519, 596), and chain shuffling (U.S. Pat. No.5,565, 332). The general recombinant DNA technology for preparation of such antibodies is also known (see European Patent Application EP 125023 and International Patent Application WO 96/02576).

The Fab of the present invention can be obtained by treating an antibody which specifically reacts with ICOS with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with ICOS with a protease, pepsin.

Also, the F(ab')2 can be produced by binding Fab' described below via a thioether bond or a disulfide bond.

The Fab' of the present invention can be obtained by treating F(ab')2 which specifically reacts with human ICOS with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. Nos. 5,859,205; 5,585,089; 4,816,567; EP0173494).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity.

In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics. In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The conservative derivatives according to the invention are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like).

Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm.

A conservative derivative according to the invention also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared. Two amino acid sequences are "substantially homologous" or "substantially similar" when greater than 80%, preferably greater than 85%, preferably greater than 90% of the amino acids are identical, or greater than about 90%, preferably grater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein. As outlined above, amino acid substitutions are generally therefore based on the relative similarity of the amino acid side-chain substituents, for example, their hydrophobicity, hydrophilicity, charge, size, and the like.

Exemplary substitutions which take various of the foregoing characteristics into consideration are well known to those of skill in the art and include: arginine and lysine; glutamate and aspartate; serine and threonine; glutamine and asparagine; and valine, leucine and isoleucine. Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N-or O-linked glycosylation. Depending on the coupling mode used, the sugar(s) may be attached to (a) arginine and histidine, (b) free carboxyl groups, (c) free sulfhydryl groups such as thoseof cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact.

Enzymatic cleavage of carbohydrate moieties on antibodies can be achieved by the use of a variety of endo-and exo-glycosidases.

Another type of covalent modification of the antibody comprises linking the antibody to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337. It may be also desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. J Exp Med. 1992 Oct. 1; 176(4):1191-5 and Shopes B. J Immunol. 1992 May 1; 148(9):2918-22).

The invention will further be illustrated in view of the following figures and example.

FIGURE LEGEND

Female immunodeficient mice (7-20 weeks NSG and NOG) were irradiated (2Gy) and engrafted with $2 \cdot 10^6$ of human PBMC by retro orbital injection. Anti-huICOS antibody (314.8) or isotype control (500 µg/mouse) was injected intraperitoneally. A. Average weight (percentage+standard deviation) for mice receiving PBMC plus control IgG (500 µg, grey line), anti-ICOS (500 µg, black line). B. Kaplan-Meier survival curves for different groups of mice as shown in (A). *Log-rank (Mantel-Cox) Test $p<0.001$ FIG. 2. 314.8 treatment reduces mononuclear cell (MNC) infiltrates in peripheral organs. Hematoxylin-eosin staining of liver (D16 post transfer) and lung (−PBMC D90, +PBMC +Iso D70, +PBMC +314.8 D98 post transfer). *$p<0.05$ Unpaired t-test.

EXAMPLE

Use of Anti-ICOS mAb 314.8 in a Murine GVHD Model

Material and Methods

Immunodeficient NOD.SCID.γc−/− (NSG) mice (from the Jackson Laboratory) were irradiated at 2 Gy before injection of $2 \cdot 10^6$ total Peripheral Blood Mononuclear cells (PBMC) from healthy donors. In these experiments, the inventors assessed weight loss and survival of injected mice overtime, as clinical parameters of GVHD appearance and severity. Weight loss was represented as the percentage of initial weight of the injected mice at different time points after PBMC injection. In some experiments, blood and spleen cells were harvested and frequencies of T cells were determined by flow cytometry using human-specific fluorescent mAbs. Five independent experiments were performed with five different human healthy PBMC donors.

Results

Figure 1:
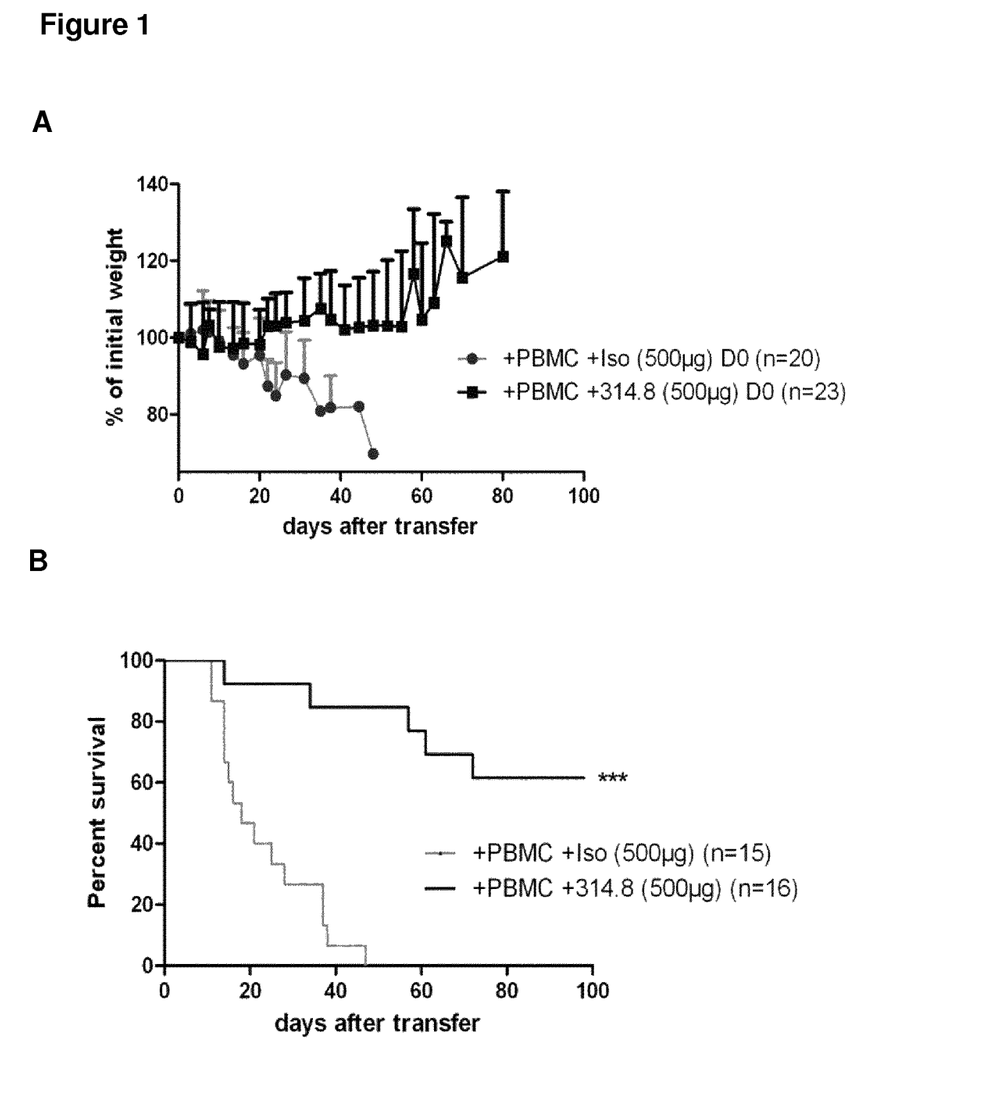
FIG. 1. Anti-huICOS (314.8) antibody prevents weight loss and improves survival during xeno-GVHD.
Figure 2:
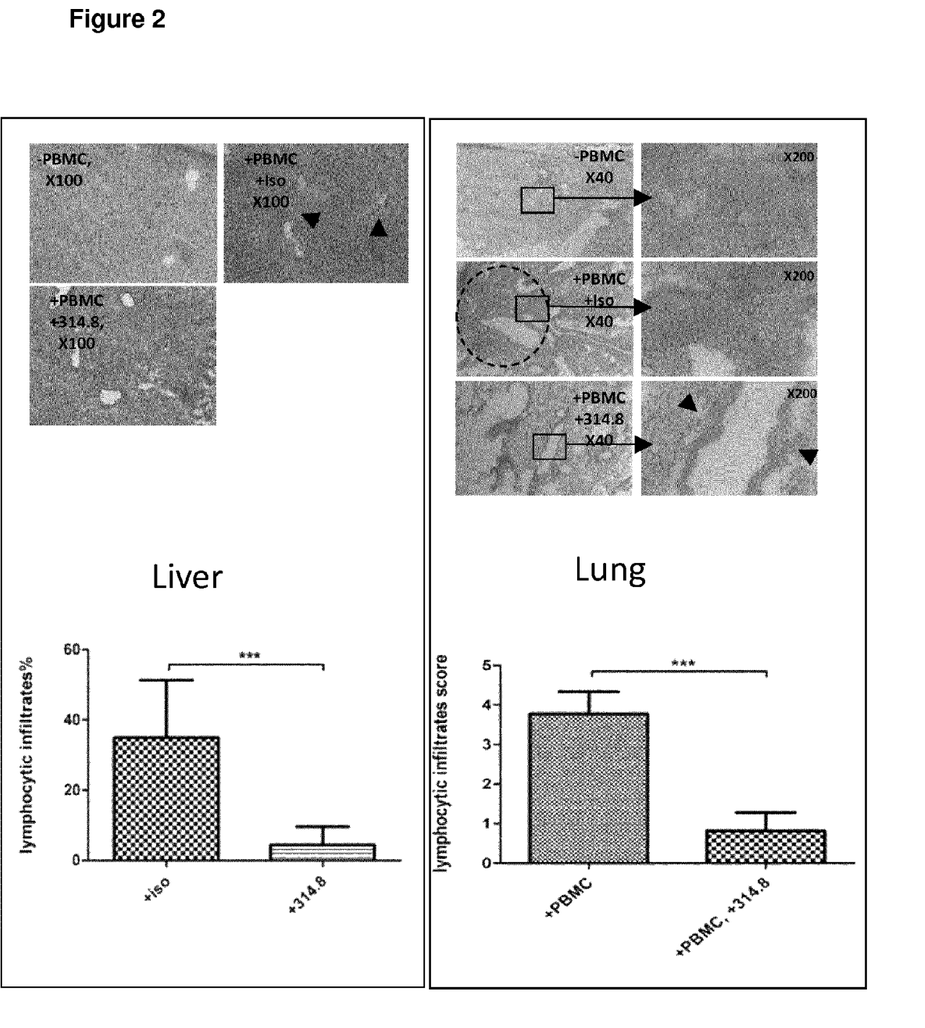
Figure 3:
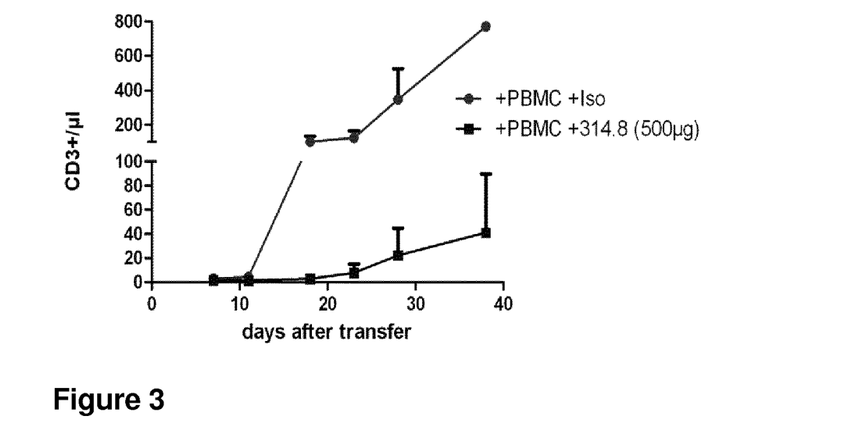
FIG. 3. anti-huICOS antibody prevents human T cells expansion in the blood. Kinetic of CD3+ T cells expansion was performed in the blood of control (n=11) and 314.8 (n=5) treated mice using the Truecount beads FIG. 4. Anti-ICOS treatment only delays the death caused by established GVHD. Dx=mice at or below 85% of IW (PBMC at DO). D8=injection of mAb relative to PBMC (D0).
Figure 4:
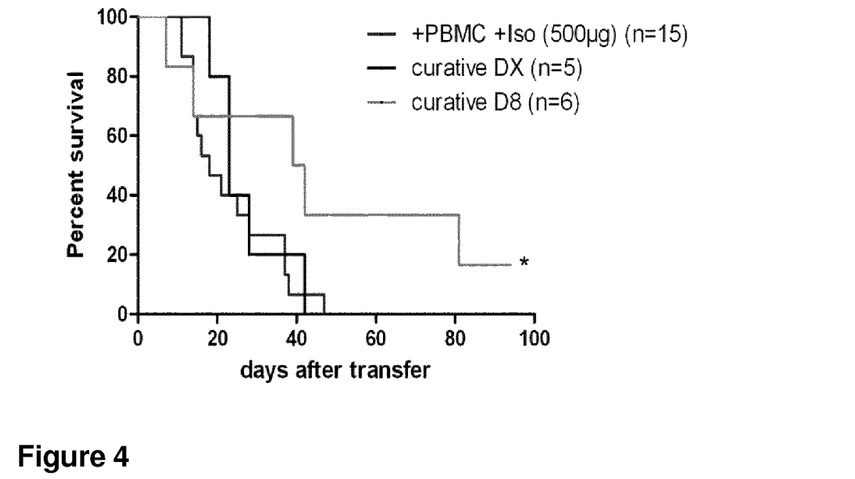

The first panel showed a rapid weight loss in mice injected with PBMC and the control irrelevant mAb compared to mice having received PBMC and the anti-ICOS mAb (FIG. 1A). This loss was accompanied by death of all mice (FIG. 1B). In contrast, 60% of anti-ICOS-treated mice survived until the end of the experiment (FIG. 1B). This protection was correlated to a lesser infiltration of mononuclear cells in the liver and in the lungs of the mice (FIG. 2). Massive infiltration were detected around vascular structures in control mice whereas very rare cells were detected in the same zone in 314.8-treated animals (FIG. 2). Visual quantification showed that the numbers of infiltrated vessels were significantly lower in the anti-ICOS treated groups. Numbers of human T cells were determined in the blood of treated animals using the TrueCount reagents at various time after injection. The results showed a massive expansion of T cells in the first month after injection in the control group. In contrast, anti-ICOS treated mice presented with a lesser numbers of T cells in the blood (FIG. 3) and in the spleen (not shown). Thus, anti-ICOS mAb prevented expansion of human T cells in the xeno-GVHD setting. Finally, after having shown that the antibody had a preventive effect on GVHD, we wanted to evaluate the curative effect of the antibody (FIG. 4). To do this, we injected mice with freshly isolated PBMC and either waited for 8 days before injecting the 314.8 antibody or until the mouse lost 85% of her initial weight. In this latter setting, mice died at the same rate and same pace than untreated controls. In contrast, the survival time was doubled in the group that received the antibody at day 8. Altogether, the results show a significant protection of the anti-ICOS mAb 314.8 against xeno-GVHD, correlated to a limited expansion of human T cells in vivo.

Furthermore, the results show that the anti-ICOS mAb represent a new therapeutic option to treat GVHD.

The invention claimed is:

1. A method for treating a graft versus host disease in a subject in need thereof, comprising
administering to said subject a therapeutically effective amount of an antibody directed against ICOS having the following 6 CDRs:

|  | Aminoacid sequence |
|---|---|
| H-CDR1 | GYTFTTYWMH (SEQ ID NO: 7) |
| H-CDR2 | EIDPSDSYVNYNQNFKG (SEQ ID NO: 8) |
| H-CDR3 | FDY (SEQ ID NO: 9) |
| L-CDR1 | RSSKSPLHSNGNIYLY (SEQ ID NO: 10) |
| L-CDR2 | RMSNLAS (SEQ ID NO: 11) |
| L-CDR3 | MQHLEYPYT (SEQ ID NO: 12). |

2. The method according to claim 1, wherein the nucleotidic sequences encoding the 6 CDRs of said antibody are the following:

|  | DNA sequence |
|---|---|
| H-CDR1 | GGCTACACCTTCACCACCTACTGGATGCAC (SEQ ID NO: 1) |
| H-CDR2 | GAGATTGATCCTTCTGATAGTTATGTTAAC TACAATCAAAACTTTAAGGGC (SEQ ID NO: 2) |
| H-CDR3 | TTTGATTAC (SEQ ID NO: 3) |
| L-CDR1 | AGGTCTAGTAAGAGTCCCCTGCATAGTAAC GGCAACATTTACTTATAT (SEQ ID NO: 4) |
| L-CDR2 | CGGATGTCCAACCTTGCCTCA (SEQ ID NO: 5) |
| L-CDR3 | ATGCAACATCTAGAATATCCGTACACG (SEQ ID NO: 6). |

3. The method according to claim 1 wherein said antibody comprises a heavy chain comprising SEQ ID NO:18 and a light chain comprising SEQ ID NO:20.

4. The method according to, claim 1, wherein said antibody is encoded by at least the nucleotidic sequence SEQ ID NO:17 for the heavy chain and at least the nucleotidic sequence SEQ ID NO:19 for the light chain.

5. The method according to claim 1, wherein said antibody is selected from the group consisting of Icos 314-8, conservative fragments of Icos 314-8 and conservative derivatives of Icos 314-8.

6. The method of claim 1, wherein the graft versus host disease is selected from the group consisting of acute fulminant graft-versus-host-disease (aGVHD) and chronic graft-versus-host-disease (cGVHD).

* * * * *

SEQUENCE LISTING

```
<160> NUMBER OF SEQ ID NOS: 20

<210> SEQ ID NO 1
<211> LENGTH: 30
<212> TYPE: DNA
<213> ORGANISM: Mus musculus

<400> SEQUENCE: 1
ggctacacct tcaccaccta ctggatgcac                                     30

<210> SEQ ID NO 2
<211> LENGTH: 51
<212> TYPE: DNA
<213> ORGANISM: Mus musculus

<400> SEQUENCE: 2
gagattgatc cttctgatag ttatgttaac tacaatcaaa actttaaggg c             51

<210> SEQ ID NO 3
<211> LENGTH: 9
<212> TYPE: DNA
<213> ORGANISM: Mus musculus

<400> SEQUENCE: 3 tttgattac                                                            9

<210> SEQ ID NO 4
<211> LENGTH: 48
<212> TYPE: DNA
<213> ORGANISM: Mus musculus

<400> SEQUENCE: 4
aggtctagta agagtcccct gcatagtaac ggcaacattt acttatat                 48

<210> SEQ ID NO 5
<211> LENGTH: 21
<212> TYPE: DNA
<213> ORGANISM: Mus musculus

<400> SEQUENCE: 5
cggatgtcca accttgcctc a                                              21
```

<210> SEQ ID NO 6
<211> LENGTH: 27
<212> TYPE: DNA
<213> ORGANISM: Mus musculus

<400> SEQUENCE: 6
atgcaacatc tagaatatcc gtacacg        27

<210> SEQ ID NO 7
<211> LENGTH: 10
<212> TYPE: PRT
<213> ORGANISM: Mus musculus

<400> SEQUENCE: 7

Gly Tyr Thr Phe Thr Thr Tyr Trp Met His
1               5                   10

<210> SEQ ID NO 8
<211> LENGTH: 17
<212> TYPE: PRT
<213> ORGANISM: Mus musculus

<400> SEQUENCE: 8

Glu Ile Asp Pro Ser Asp Ser Tyr Val Asn Tyr Asn Gln Asn Phe Lys
1               5                   10                  15
Gly

<210> SEQ ID NO 9
<211> LENGTH: 3
<212> TYPE: PRT
<213> ORGANISM: Mus musculus

<400> SEQUENCE: 9

Phe Asp Tyr
1

<210> SEQ ID NO 10
<211> LENGTH: 16
<212> TYPE: PRT
<213> ORGANISM: Mus musculus

<400> SEQUENCE: 10

Arg Ser Ser Lys Ser Pro Leu His Ser Asn Gly Asn Ile Tyr Leu Tyr
1               5                   10                  15

<210> SEQ ID NO 11
<211> LENGTH: 7
<212> TYPE: PRT
<213> ORGANISM: Mus musculus

<400> SEQUENCE: 11

Arg Met Ser Asn Leu Ala Ser
1               5

<210> SEQ ID NO 12
<211> LENGTH: 9
<212> TYPE: PRT
<213> ORGANISM: Mus musculus

<400> SEQUENCE: 12

Met Gln His Leu Glu Tyr Pro Tyr Thr
1               5

<210> SEQ ID NO 13

<211> LENGTH: 426
<212> TYPE: DNA
<213> ORGANISM: Mus musculus

<400> SEQUENCE: 13

```
atgggatggc gctgtatcat cctcttcttg gtatcaacag ctacaggtgt ccactcccag      60
gtccaactac agcagcctgg gactgaactt atgaagcctg ggcttcagt gaagctgtcc      120
tgcaaggctt ctggctacac cttcaccacc tactggatgc actgggtgaa gcagaggcct      180
ggacaaggcc ttgagtggat cggagagatt gatccttctg atagttatgt taactacaat      240
caaaacttta agggcaaggc cacattgact gtagacaaat cctccagcac agcctacata      300
cagctcagca gcctgacatc tgaggactct gcggtctatt tttgtgcgag atcccctgat      360
tactacggta ctagtcttgc ctggtttgat tactggggcc aagggactct ggtcactgtc      420
tctaca                                                                426
```

<210> SEQ ID NO 14
<211> LENGTH: 142
<212> TYPE: PRT
<213> ORGANISM: Mus musculus

<400> SEQUENCE: 14

```
Met Gly Trp Arg Cys Ile Ile Leu Phe Leu Val Ser Thr Ala Thr Gly
1               5                   10                  15

Val His Ser Gln Val Gln Leu Gln Gln Pro Gly Thr Glu Leu Met Lys
            20                  25                  30

Pro Gly Ala Ser Val Lys Leu Ser Cys Lys Ala Ser Gly Tyr Thr Phe
        35                  40                  45

Thr Thr Tyr Trp Met His Trp Val Lys Gln Arg Pro Gly Gln Gly Leu
    50                  55                  60

Glu Trp Ile Gly Glu Ile Asp Pro Ser Asp Ser Tyr Val Asn Tyr Asn
65                  70                  75                  80

Gln Asn Phe Lys Gly Lys Ala Thr Leu Thr Val Asp Lys Ser Ser Ser
                85                  90                  95

Thr Ala Tyr Ile Gln Leu Ser Ser Leu Thr Ser Glu Asp Ser Ala Val
            100                 105                 110

Tyr Phe Cys Ala Arg Ser Pro Asp Tyr Tyr Gly Thr Ser Leu Ala Trp
        115                 120                 125

Phe Asp Tyr Trp Gly Gln Gly Thr Leu Val Thr Val Ser Thr
    130                 135                 140
```

<210> SEQ ID NO 15
<211> LENGTH: 396
<212> TYPE: DNA
<213> ORGANISM: Mus musculus

<400> SEQUENCE: 15

```
atgaggtgcc tagctgagtt cctggggctg cttgtgctct ggatccctgg agtcattggg      60
gatattgtga tgactcaggc tgcaccctct gtacctgtca ctcctggaga gtcagtatcc     120
atctcctgca ggtctagtaa gagtcccctg catagtaacg gcaacattta cttatattgg     180
ttcctgcaga ggccaggcca gtctcctcag ctcctgatat atcggatgtc caaccttgcc     240
tcaggagtcc cagacaggtt cagtggcagt gggtcaggaa ctactttcac actgaaaatc     300
agtagagtgg aggctgagga tgtgggtgtt tattactgta tgcaacatct agaatatccg     360
tacacgttcg gagggggac caagctggaa ataaaa                               396
```

<210> SEQ ID NO 16
<211> LENGTH: 132
<212> TYPE: PRT
<213> ORGANISM: Mus musculus

<400> SEQUENCE: 16

Met Arg Cys Leu Ala Glu Phe Leu Gly Leu Leu Val Leu Trp Ile Pro
1               5                   10                  15

Gly Val Ile Gly Asp Ile Val Met Thr Gln Ala Ala Pro Ser Val Pro
            20                  25                  30

Val Thr Pro Gly Glu Ser Val Ser Ile Ser Cys Arg Ser Ser Lys Ser
        35                  40                  45

Pro Leu His Ser Asn Gly Asn Ile Tyr Leu Tyr Trp Phe Leu Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Thr Phe
                85                  90                  95

Thr Leu Lys Ile Ser Arg Val Glu Ala Glu Asp Val Gly Val Tyr Tyr
            100                 105                 110

Cys Met Gln His Leu Glu Tyr Pro Tyr Thr Phe Gly Gly Gly Thr Lys
        115                 120                 125

Leu Glu Ile Lys
    130

<210> SEQ ID NO 17
<211> LENGTH: 369
<212> TYPE: DNA
<213> ORGANISM: Mus musculus

<400> SEQUENCE: 17
caggtccaac tacagcagcc tgggactgaa cttatgaagc ctggggcttc agtgaagctg      60
tcctgcaagg cttctggcta caccttcacc acctactgga tgcactgggt gaagcagagg     120
cctggacaag gccttgagtg gatcggagag attgatcctt ctgatagtta tgttaactac     180
aatcaaaact ttaagggcaa ggccacattg actgtagaca atcctccag cacagcctac     240
atacagctca gcagcctgac atctgaggac tctgcggtct attttgtgc gagatcccct     300
gattactacg gtactagtct tgcctggttt gattactggg gccaagggac tctggtcact     360
gtctctaca                                                            369

<210> SEQ ID NO 18
<211> LENGTH: 123
<212> TYPE: PRT
<213> ORGANISM: Mus musculus

<400> SEQUENCE: 18

Gln Val Gln Leu Gln Gln Pro Gly Thr Glu Leu Met Lys Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Val Asn Tyr Asn Gln Asn Phe
    50                  55                  60

Lys Gly Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Phe Cys
                85                  90                  95

Ala Arg Ser Pro Asp Tyr Tyr Gly Thr Ser Leu Ala Trp Phe Asp Tyr
            100                 105                 110

Trp Gly Gln Gly Thr Leu Val Thr Val Ser Thr
        115                 120

<210> SEQ ID NO 19
<211> LENGTH: 336
<212> TYPE: DNA
<213> ORGANISM: Mus musculus

<400> SEQUENCE: 19
gatattgtga tgactcaggc tgcaccctct gtacctgtca ctcctggaga gtcagtatcc      60
atctcctgca ggtctagtaa gagtcccctg catagtaacg gcaacattta cttatattgg     120
ttcctgcaga ggccaggcca gtctcctcag ctcctgatat atcggatgtc caaccttgcc    180
tcaggagtcc cagacaggtt cagtggcagt gggtcaggaa ctactttcac actgaaaatc    240
agtagagtgg aggctgagga tgtgggtgtt tattactgta tgcaacatct agaatatccg    300
tacacgttcg agggggggac caagctggaa ataaaa                              336

<210> SEQ ID NO 20
<211> LENGTH: 112
<212> TYPE: PRT
<213> ORGANISM: Mus musculus

<400> SEQUENCE: 20

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Pro Leu His Ser
            20                  25                  30

Asn Gly Asn Ile Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Thr Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110